(12) United States Patent
Zeng et al.

(10) Patent No.: US 9,987,229 B2
(45) Date of Patent: *Jun. 5, 2018

(54) PROCESS FOR PREPARING A MEDICAMENT

(71) Applicant: Norton Healthcare Ltd., London (GB)

(72) Inventors: Xian-Ming Zeng, London (GB); Seah Kee Tee, London (GB)

(73) Assignee: Norton Healthcare Ltd., London (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/453,940

(22) Filed: Mar. 9, 2017

(65) Prior Publication Data

US 2017/0172925 A1 Jun. 22, 2017

Related U.S. Application Data

(60) Continuation of application No. 15/137,671, filed on Apr. 25, 2016, now Pat. No. 9,616,024, which is a division of application No. 10/594,473, filed as application No. PCT/US2004/028345 on Sep. 1, 2004, now Pat. No. 9,345,664.

(60) Provisional application No. 60/499,582, filed on Sep. 2, 2003.

(51) Int. Cl.
| | |
|---|---|
| *A61K 9/14* | (2006.01) |
| *A61M 15/00* | (2006.01) |
| *A61K 31/58* | (2006.01) |
| *A61K 9/00* | (2006.01) |
| *A61K 31/167* | (2006.01) |
| *A61K 31/137* | (2006.01) |
| *A61K 9/16* | (2006.01) |
| *A61K 31/56* | (2006.01) |

(52) U.S. Cl.
CPC .......... *A61K 9/1623* (2013.01); *A61K 9/0075* (2013.01); *A61K 31/167* (2013.01); *A61K 31/56* (2013.01); *A61K 31/58* (2013.01)

(58) Field of Classification Search
None
See application file for complete search history.

(56) References Cited

U.S. PATENT DOCUMENTS

| | | | |
|---|---|---|---|
| 3,957,965 A | | 5/1976 | Hartley et al. |
| 4,161,516 A | | 7/1979 | Bell |
| 5,518,998 A | * | 5/1996 | Backstrom .......... A61K 9/0075 424/489 |
| 6,030,604 A | | 2/2000 | Trofast |
| 6,045,828 A | * | 4/2000 | Bystrom .............. A61K 9/0075 424/404 |
| 6,371,171 B1 | | 4/2002 | Trofast et al. |
| 2002/0106332 A1 | | 8/2002 | Walz et al. |
| 2003/0068278 A1 | | 4/2003 | Boeck et al. |

FOREIGN PATENT DOCUMENTS

| | | |
|---|---|---|
| GB | 1242211 | 8/1971 |
| WO | 9500128 | 1/1995 |
| WO | 9521015 | 8/1995 |
| WO | 0230390 | 4/2002 |
| WO | 03024396 | 3/2003 |
| WO | 2004017918 | 3/2004 |

OTHER PUBLICATIONS

Ikegami, et al., "In vitro inhalation behavior of spherically agglomerated steroid particles with carrier lactose," Advanced Powder Technology, (2000) 11: 323-332.
Ikegami, et al., "Simultaneous particulate design of primary and agglomerated crystals of steroid by spherical agglomeration in liquid for dry powder inhalation," Powder Technology, (2003) 130: 290-297 (including preface).
De Villiers, et al., "Dissolution rate a measurement of the deaggregation of furosemide agglomerates during an interactive mixing process," Drug Development and Industrial Pharmacy (1990) 16: 1391-1397.
Cartilier, et al., "Effect of flowing adjuvants on the homogeneity and the kinetics of mixing of low dosage cohesive powder mixtures," Drug Development and Industrial Pharmacy (1986) 12: 1203-1218.
De Villiers, "Description of the kinetics of the deagglomeration of drug particle agglomerates during powder mixing," International Journal of Pharmaceutics (1997) 151: 1-6.
Vazquez, et al., "Assessment of the bronchodilator effect of inhaled furosemide compared to salbutamol in asthmatic patients," J Invest Allergol Clin Immunol (1998) 8: 115-118.
Begat, et al., "The role of force control agents in high-dose dry powder inhaler formulations," American Pharmacists Association J Pharma Sci (2009) 98: 2770-2783.
Morishima, et al., "Micromeritic characteristics and agglomeration mechanisms in the spherical crystallization of bucillamine by the spherical agglomeration and the emulsion solvent diffusion methods," Powder Technology, (1993) 76: 57-64.
Letter from Norton Healthcare Ltd. to Dr. Zeng, dated Aug. 25, 1998.

(Continued)

*Primary Examiner* — Robert A Wax
*Assistant Examiner* — Randeep Singh
(74) *Attorney, Agent, or Firm* — Morgan, Lewis & Bockius LLP (57) ABSTRACT

The present invention provides a process for preparing a particulate medicament that has greater homogeneity and a lower adhesion between the particles of the active ingredient and the carrier. The process comprises the steps of: (a) combining a pharmaceutically active ingredient in the form of an agglomerate of primary particles having an agglomerate particle size such that the agglomerate is capable of passing through a sieve having a mesh of 50-3000 .mu.m with a pharmaceutically acceptable particulate carrier, and (b) mixing the resultant material in a mixer to break up the agglomerate into primary particles dispersed in the pharmaceutically acceptable particulate carrier such that 90% or more of the pharmaceutically active ingredient exists as primary particles having a particle size of 50 .mu.m or less.

12 Claims, 5 Drawing Sheets

(56) References Cited

OTHER PUBLICATIONS

Acceptance signed by Dr. Zeng, dated Aug. 28, 1998.
"The Mechanics of Inhaled Pharmaceutical Aerosols, An Introduction," Ed. W.H. Finlay, Academic Press (2001), pp. 148-149.
Application for an Injunction for Patent Infringement filed by Norton Healthcare in Poland, dated Dec. 22, 2014.
Decision on Transferring, dated Jan. 7, 2015.
Delivery of Decision, dated Jan. 9, 2015.
Clarke, et al., "The formulation of powder inhalation systems containing a high mass of nedocromil sodium trihydrate," J Pharm Sci (2001) 90: 213-223.
Cartilier et al., "Effect of drug agglomerates upon the kinetics of mixing of low dosage cohesive powder mixtures," Drug Development and Industrial Pharmacy (1989) 15: 1911-1931.
Experimental Report of Mr. Kyrre Thalberg, dated Apr. 1, 2015.
Supplementary Declaration of Mr. Kyrre Thalberg, dated Dec. 22, 2015.

* cited by examiner

PROCESS FOR PREPARING A MEDICAMENT

CROSS-REFERENCE TO RELATED APPLICATIONS

This application is a continuation of U.S. patent application Ser. No. 15/137,671, filed Apr. 25, 2016, which is a divisional of U.S. patent application Ser. No. 10/594,473, filed Nov. 13, 2007, which issued as U.S. Pat. No. 9,345,664 on May 24, 2016, which is the U.S. National Stage Application of International Patent Application No. PCT/US2004/028345, filed Sep. 1, 2004, which claims the benefit of U.S. Provisional Application No. 60/499,582, filed Sep. 2, 2003, the entirety of which are incorporated herein by reference.

TECHNICAL FIELD OF THE INVENTION

The invention relates to a process for preparing a particulate medicament, and to a process for dispersing an active pharmaceutical ingredient in a pharmaceutically acceptable particulate carrier.

BACKGROUND OF THE INVENTION

Dispersed powders of an active pharmaceutical ingredient in a pharmaceutically acceptable particulate carrier have wide applicability in the pharmaceuticals sector. They have particular importance in the area of inhalable compositions. In order to be able to be inspired into the key target sites in the lungs of patients, inhalation drugs are typically provided in micronised form with average particle sizes of up to 10 microns. A number of devices have been developed for assisting the delivery of such medicaments into the lungs of patients. In one sort of device, a dry powdered inhaler (DPI) device, the medicament to be inhaled is dispensed into an air stream produced by the inspiratory action of the patient. A large number of such devices have been developed. The device may be a single dose device (e.g. wherein drug is dispensed from a pre-metered dosage means such as a capsule) or multidose (where the drug is stored in a reservoir and then metered prior to dispersal in the air stream or the drug is pre-metered and stored in multiple dosage packs such as blisters). In many DPI devices, the particulate drug is mixed with an excipient powder of larger average particle size and the drug particles are blended with the excipient to create a fairly homogenous mixture. The larger particle size of the excipient results in the powder mixture being flowable, and the homogeneity of the mixture enable it to be metered into accurately measurable doses. This is of particular importance when only very small quantities of the drug are required in a dose. Excipient powders of this kind, and pharmaceutical powder compositions for inhalation utilising such excipients are described, for example, in U.S. Pat. No. 3,957,965.

The flow properties of the powder can be improved by controlled agglomeration of the powder. GB 1,569,911 discloses a process for the agglomeration of a drug into soft pellets using a binder to produce a paste, which is extruded through a sieve to create agglomerates. The formation of soft pellets allows diluents, such as coarse lactose, to be omitted from the composition. U.S. Pat. No. 4,161,516 also discloses the formation of soft drug pellets used to improve flowability. U.S. Pat. No. 6,371,171 discloses the preparation of spheronised agglomerates which have sufficient strength to withstand processing and packaging but which are sufficiently soft to de-agglomerate into primary particles during delivery through a breath-actuated inhaler. Examples of ingredients disclosed in U.S. Pat. No. 6,371,171, which may be formed into spheronised agglomerates, are terbutaline, budesonide and lactose.

However, there is still a need in the art for powders having improved dispersion of the pharmaceutically active ingredient in the pharmaceutically acceptable particulate carrier and with improved activity of the active ingredient.

SUMMARY OF THE INVENTION

The present invention provides a process for preparing a particulate medicament that has greater homogeneity and a lower adhesion between the particles of the active ingredient and the carrier. The invention additionally provides medicaments and dispensing devices using medicaments prepared by the processes of the invention.

BRIEF DESCRIPTION OF THE DRAWINGS

The present invention will now be described with reference to the drawings in which.

DETAILED DESCRIPTION OF THE INVENTION

The present invention provides a process for preparing a particulate medicament that has greater homogeneity and a lower adhesion between the particles of the active ingredient and the carrier. The process for preparing a medicament comprises the steps of: (a) combining a pharmaceutically active ingredient in the form of an agglomerate of primary particles having an agglomerate particle size such that the agglomerate is capable of passing through a sieve having a mesh of 50-3000 μm with a pharmaceutically acceptable particulate carrier, and (b) mixing the resultant material in a mixer to break up the agglomerate into primary particles dispersed in the pharmaceutically acceptable particulate carrier such that 90% or more of the pharmaceutically active ingredient exists as primary particles having a particle size of 50 μm or less. The invention additionally provides medicaments and dispensing devices using medicaments prepared by the processes of the invention.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined.

Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001).

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used in this specification, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, unless specifically indicated otherwise, the word "or" is used in the "inclusive" sense of "and/or" and not the "exclusive" sense of "either/or."

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defused by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

One aspect of the invention provides a process for preparing a medicament comprising the steps of (a) combining a pharmaceutically active ingredient in the form of an agglomerate of primary particles having an agglomerate particle size such that the agglomerate is capable of passing through a sieve having a mesh of 50-3000 μm with a pharmaceutically acceptable particulate carrier, and (b) mixing the resultant material in a mixer to break up the agglomerate into primary particles dispersed in the pharmaceutically acceptable particulate carrier such that 90% or more of the pharmaceutically active ingredient exists as primary particles having a particle size of 50 μm or less.

The active ingredient is dispersed in the carrier, but prior to dispersion, the active ingredient must be formulated so that it is in the form of a loose agglomerate. That is, the agglomerate must be capable of being broken down into primary particles such that 90% or more of the pharmaceutically active ingredient exists in the dispersion as primary particles having a particle size of 50 μm or less by mixing with the carrier in a mixer using conventional mixing techniques. By "primary particles", it is meant particles of the loose agglomerate that have been broken down by mixing and may still include aggregates, albeit reduced in size from the original loose agglomerates.

In order to provide a uniform dispersion of the active ingredient in the carrier, prior to mixing, the active ingredient (in the fouls of the loose agglomerate) has a particle size such that it is capable of passing through a sieve having a mesh of 50-3000 μm. One way of achieving such a particle size is to pass the loose agglomerate through such a sieve, although other methods of obtaining such particle sizes are known in the art, for example by granulation. Sieving the loose agglomerate is described.

In some embodiments of this aspect, the particle size of the loose agglomerate for the active ingredient is such that it is capable of passing through a sieve having a mesh of 150 to 2000 μm. In other embodiments, the particle size the loose agglomerate is such that it is capable of passing through a sieve having a mesh of 250 to 1000 μm, more preferably 250 to 500 μm. It is particularly preferable to pass the loose agglomerate through a sieve having a mesh size of 250 or 355 μm.

Sieving may be carried out on the dry loose agglomerate or, alternatively, a liquid carrier (or medium) may be used. A liquid carrier is particularly useful where the loose agglomerate is being passed through a sieve having a small mesh size. Suitable liquid carriers include liquefied gases such as liquid nitrogen and supercritical fluids such as supercritical carbon dioxide.

In step (a), the pharmaceutically active ingredient in the form of a loose agglomerate is combined with a pharmaceutically acceptable particulate carrier. In step (b), the combined components of step (a) are mixed in order to break down the loose agglomerate. Mixing may be carried out using any conventional mixer. However, the mixer must have sufficient shear so that the mixed agglomerate is broken down such that 90% or more of the pharmaceutically active ingredient exists as primary particles as defined herein having a particle size of 50 μm or less.

The particle size of the primary particles size of the mixed agglomerate is 90% or more having a particle size of 50 μm or less (not including zero), i.e. $d_{90}$<50 μm. The particle size is preferably 20 μm or less, and particularly 10 μm or less. In other embodiments, the primary particle size range is from about 2 to about 5 μm. Where the medicament is an inhalable medicament the required size of the primary particles will be dependent on the area of the lungs being targeted. Medicaments targeting the upper airways will have a particle size of 10-20 μm whereas medicaments targeting the lower airways will have a particle size of 5 μm or less, e.g. 1-5 μm. The minimum size of the primary particles is less important but they are preferably 0.5 μm or greater.

In some embodiments, 95% or more of the primary particles satisfy these conditions. The particle size of the primary particles in the formulation may be determined using optical or scanning electron microscopy or other appropriate techniques.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

The process of the present invention produces a highly homogeneous dispersion. The homogeneity of the resultant particulate material may be determined, for example, by HPLC. A plurality of samples is taken from the resultant particulate material, preferably greater than 10 samples are taken. HPLC is then used to determine the amount of drug in each sample. The relative standard deviation (RSD) around the mean value is determined and preferably the RSD is less than or equal to 5%. A lower RSD of the blend results in a higher uniformity of the delivered dose, which is useful from a clinical and regulatory perspective.

A high velocity of shear mixing provides the energy required to produce the rapid dispersion of drug particles such that a homogeneous mixture is formed more quickly. Excessive mixing should, however, be avoided to prevent demixing of the formulation resulting from the binding of the drug to the carrier on account of a build up of interparticulate forces.

It has also been found that the process of the present invention produces a particulate material having a lower adhesion between the active ingredient and the carrier than in conventional processes. This is partly attributable to the relatively low energy input required to make a homogenous blend from the loose agglomerates of the drug. In the case of an inhalable medicament for example, a lower adhesion provides a higher portion of drug that can be delivered to the lower respiratory tract, leading to a potentially higher therapeutic effect and a potentially lower toxicity.

The amount of drug delivered to the lower respiratory tract may be approximated using a Twin Stage Impinger (TSI). The TSI is divided in to three stages, namely an adapter which represents the mouth piece, a first stage which represents upper airways, and a second stage which represents the lower airways. The cut off particle diameter between the first and second stage is about 6.4 µm. The fine particle fraction (FPF) provides a measure of the amount of the drug which reaches the lower airways and is defined as the % of drug deposited in the lower stage compared to the total drug delivered. It has been found that the FPF is improved by using aggregates which have been sieved using a 355 µm sieve prior to mixing compared to sieves having other sizes.

Since the formation of aggregates is common to substantially all particulate medicaments, the present invention is not restricted to any particular pharmaceutically active ingredient. In addition, homogeneous blends are applicable to a wide variety of formulations including inhalable medicaments, capsules and tablets. However, the present invention is described for inhalable medicaments.

In embodiments of the invention, the inhalable medicament(s) are anti-inflammatory steroids and bronchodilators, while in other embodiments; the inhalable medicament is budesonide, formoterol or etiprednol dicloacetate. In addition, mixtures of active ingredients could be formulated in accordance with the present invention.

The compositions according to the invention are optionally formulated in a pharmaceutically acceptable vehicle with any of the well-known pharmaceutically acceptable carriers, including diluents and excipients (see *Remington's Pharmaceutical Sciences*, 18$^{th}$ Ed., Gennaro, Mack Publishing Co., Easton, Pa. 1990 and *Remington: The Science and Practice of Pharmacy*, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic.

As used herein, "medicament" or "active ingredient" is meant to encompass active pharmaceuticals appropriate for inhalation therapy in dry powder form. Representative, non-limiting examples include bronchodilators (e.g., epinephrine, metaproterenol, terbutaline, albuterol, and the like), anticholinergic agents (e.g., ipratropium bromide), xanthines (e.g., aminophylline, dyphylline, aminophylline), inhalant corticosteroids (e.g., flunisolide, beclomethasone, budesonide, and the like), or β-2 adrenergic receptor agonists (e.g., salmeterol and formoterol).

The active ingredient may be in any isomeric form or mixture of isomeric forms, for example a pure enantiomer, a mixture of enantiomers, a racemate or a mixture thereof where applicable. Pharmaceutically acceptable derivatives including pharmaceutically acceptable salts, in particular acid addition salts with inorganic acids such as hydrochloric acid, hydrobromic acid, sulphuric or phosphoric acid are also applicable. The salt may also be with an organic acid such as acetic, succinic, maleic, fumaric, citric, tartaric, and lactic or benzoic. The active ingredient and pharmaceutically acceptable derivatives thereof may exist in the form of a solvate, including the hydrate.

Similarly, the present invention is applicable to substantially all pharmaceutically acceptable particulate carriers, such as lactose, sucrose, glucose, sorbitol, mannitol, xylitol, HPMC and PEG. Preferably, the carrier is lactose, more preferably alpha-lactose monohydrate. The particle size of the particulate carrier may be varied depending on the particular application. The particle size may be anywhere from 1 µm to one or more centimeters. A preferred range is, however, 1-1000 µm, more preferably 5 to 500, more preferably 40 to 150, most preferably 40 to 90 µm. A characteristic coarse lactose is that supplied as classified lactose that is collected on a mesh with mesh size of 63 µm after passing through a mesh with mesh size of 90 µm.

The formulations of the compositions of the invention may conveniently be presented in unit dosage form and may be prepared by conventional pharmaceutical techniques. Such techniques include the step of bringing into association the compound of the invention and the pharmaceutically acceptable carrier(s), or an excipient. In general, the formulations are prepared by uniformly and intimately bringing into association the active ingredient with finely divided solid carriers, and then, if necessary, preparing discrete dosage units of the product.

The dry powder composition may be metered and filled into capsules, e.g., gelatin or hydroxypropyl methylcellulose capsules, such that the capsule contains a unit dose of active ingredient.

The present invention also provides a medicament obtainable by the process defined herein. The medicament per se, according to the present invention, has increased homogeneity and reduced active ingredient-carrier adhesion compared to known particulate medicaments and hence is distinct from known particulate medicaments.

Where the particulate medicament is formulated as an inhalable medicament, the inhalable medicament may be used for the treatment of chronic obstructive pulmonary disease. Accordingly, an aspect of the present invention further provides a dry-powder inhaler containing the particulate medicament as defined above.

In general, the active ingredient is present in the dry powder composition at an amount which is less than 10%, preferably less than 2% and most preferably, less than 1% based on the total weight of the powder. The actual amount of active ingredient in the composition will depend on the nature of the dry powder and the quantity of composition that is required for each dose. The dry powder composition may be metered and filled into capsules, e.g. gelatine or hydroxypropyl methyl cellulose capsules such that the capsule contains a unit dose of active ingredient.

When the dry powder is in a capsule containing a unit dose of active ingredient, the total amount of composition will depend on the size of the capsules and the characteristics of the inhalation device with which the capsules are being used. However, characteristic total fill weights of dry powder to per capsule are between 1 and 25 mg, e.g. 5, 10, 15 or 20 mg. Alternatively, the dry powder composition according to the invention may be filled into the reservoir of a multidose dry powder inhaler, for example of the kind illustrated in WO 92/10229.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Budesonide-Lactose Formulations

Budesonide, a hydrophobic molecule, has traditionally been found to be difficult to form homogenous blends with a hydrophilic excipient, such as lactose monohydrate. A high shear mixer is usually required to make blends containing budesonide. This example describes how controlled agglomeration of budesonide by passing it through a sieve having a mesh size of 250 µm improves the mixing homogeneity of budesonide with excipient.

Briefly, the procedure entailed combining coarse lactose monohydrate (sieved fraction of 63-90 µm) and micronised budesonide (<10 µm) to form a blend mass of 50 g (target blend strength 9.6 wt. %). The blend mass was then mixed geometrically followed by tumbling mixing (with shear bar) on the Turbula T2C (TURBULA®, Glen Creston, N.J., JUSA) at Gear 3 for 10 minutes (a low shear mixer).

Budesonide was either allowed to pass through a mesh of 250 µm prior to blending and/or the blends were passed through a mesh of 355 µm. Ten samples were taken from each blend for the analysis of content uniformity. The results are shown in Table 1.

TABLE 1

Content homogeneity results of budesonide blends

| Blends | Sieving Active | Sieving Blend | Mean/ wt. % | % RSD | Recovery/ % |
|---|---|---|---|---|---|
| Blend-1 | Yes | No | 8.50 | 4.6 | 88.5 |
| Blend-2 | No | No | 7.64 | 14.3 | 79.6 |
| Blend-3 | Yes | Yes | 7.87 | 1.5 | 82.0 |
| Blend-4 | No | Yes | 5.86 | 7.1 | 61.0 |

Table 1 shows the mean drug recovery (wt. %), the relative standard deviation and the percentage drug recovery. The reduced drug recovery in this example may be attributed to the small scale (50 g blend mass) and due to a high percentage of drug being retained by container surfaces. However, the results show the comparison between Blends 1 and 3 (of the invention) where the active ingredient was sieved and Blends 2 and 4 (comparative) where the active ingredient was not sieved. The controlled agglomeration of budesonide by sieving it through a sieve of 250 µm results in improved drug recovery and homogeneity of the blends such that it is now possible to manufacture homogeneous budesonide-lactose blends using low-shear mixers.

Example 2

Formoterol-Lactose Formulation

Unlike budesonide, formoterol is a hydrophilic molecule. It has been found that formoterol (as fumarate dihydrate) can readily form homogeneous blends with lactose monohydrate even when mixing with a low shear mixer such as the Turbula. This example shows that the results obtained with the budesonide formulations in Example 1 are also applicable for formoterol-lactose formulations.

Briefly, the procedure entailed combining coarse lactose monohydrate (sieved fraction of 63-150 µm) and micronised formoterol fumarate dihydrate (<10 µm) to form a blend mass of 100 g (target blend strength 0.265 wt. %). The blend mass was then mixed geometrically followed by tumbling mixing (with shear bar) on the Turbula T2C at Gear 3 for 10 minutes (a low shear mixer). Prior to blending with lactose, the formoterol was either non-sieved or sieved through a 250 µm sieve. Ten samples were taken from each blend for the analysis of content uniformity. The results are shown in Table 2.

TABLE 2

Content Homogeneity Results of Two Formoterol Blends

| Blends | Formoterol | Mean/ wt. % | % RSD | Recovery/ % |
|---|---|---|---|---|
| Blend-1 | Non-sieved | 0.243 | 1.2 | 91.4 |
| Blend-2 | Sieved | 0.261 | 0.9 | 99.6 |

Similar to the case of the budesonide-lactose formulation, sieving the formoterol API improved both recovery and content homogeneity of the blends.

Example 3

This study examined the effects on the performance of etiprednol dicloacetate in a multidose dry powder inhaler (MDPI).

This example relates to the conventional means to increase the fine particle fraction (FPF) of etiprednol dicloacetate MDPI. Initial studies indicate that etiprednol dicloacetate (EDA) MDPI produced a mean FPF which was only half that of budesonide MDPI using similar formulations.

A 2×2 factorial design was used to investigate the effect of formulation and process on the performance of EDA MDPI. Two batches of lactose were used for manufacturing EDA-lactose formulations and Batch 2 contained more fine lactose particles than the Batch 1.

A low and high-shear mixing regime was employed to manufacture the blend. The results are shown in Table 3.

TABLE 3

Results from 2X2 factorial design studies

| Blend | Formulation | Process | Mean emitted dose/μg | % RSD of emitted dose | FPF (%) |
|---|---|---|---|---|---|
| 1 | Batch 1 lactose | High Shear Mixing | 195.3 | 3.0 | 23 |
| 2 | Batch 2 lactose | High Shear Mixing | 182.9 | 10.6 | 27 |
| 3 | Batch 1 lactose | Low Shear Mixing | 185.3 | 5.4 | 31 |
| 4 | Batch 2 lactose | Low Shear Mixing | 168.4 | 4.9 | 37 |

The results show that changing from Batch 1 to Batch 2 lactose led to an absolute increase of 3-6% in FPF; changing from high to low shear mixing resulted in an absolute increase of 8-10% in FPF; and blends made by low shear mixing require a slightly higher drug concentration to achieve the target emitted dose (200 μg).

Example 4

This example was directed to increasing the fine particle fraction of etiprednol dicloacetate MDPI by controlled agglomeration of the active material.

Example 3 showed that the range in which to optimise the formulation is limited since further increasing the fine particle lactose is likely to reduce the dose content uniformity of the final products.

Briefly, the procedure used entailed combining coarse lactose monohydrate (sieved fraction of 63-150 μm) and micronised EDA (<10 μm) to form controlled agglomerates of <250 μm in size. The blend mass was then mixed by low shear tumbling mixing on the Turbula T2C at Gear 3 for 20 minutes (a low shear mixer). The resultant blend was then sieved <355 μm.

The results are shown in Tables 4 and 5.

TABLE 4

Homogeneity results of five batches of EDA-lactose blends

| Blend | Target EDA Conc. wt. % | Measured mean EDA Conc./wt. % | % RSD | % Recovery |
|---|---|---|---|---|
| 03-PRD-EDA-Blend-19 | 5.0 | 4.7 | 0.7 | 94.0 |
| 03-PRD-EDA-Blend-23 | 5.0 | 4.6 | 1.4 | 92.0 |
| 03-PRD-EDA-Blend-25 | 4.8 | 4.5 | 2.2 | 93.8 |
| 03-PRD-EDA-Blend-27 | 4.8 | 4.4 | 2.0 | 91.7 |
| 03-PRD-EDA-Blend-29 | 5.0 | 4.6 | 3.9 | 92.0 |

TABLE 5

Results of five batches manufactured using identical conditions

| Blends | No. of devices | Mean DPA/μg | DPA variability/% RSD | FPF/ % |
|---|---|---|---|---|
| 03-PRD-EDA-Blend-19 | 3 | 208.9 | 8.3 | 51 |
| 03-PRD-EDA-Blend-23 | 3 | 204.6 | 8.3 | 58 |
| 03-PRD-EDA-Blend-25 | 3 | 190.7 | 11.1 | 65 |
| 03-PRD-EDA-Blend-27 | 3 | 198.7 | 10.9 | 59 |
| 03-PRD-EDA-Blend-29 | 3 | 203.3 | 8.5 | 55 |

The results indicate that the controlled agglomeration of etiprednol dicloacetate results in a marked increase in the FPF of the drug. The process was reproducible with drug recovery ranging between 92% and 96%. Dose delivery was highly consistent with overall RSD less than 10%.

Example 5

This example was directed to visualizing (by SEM) the micronised etiprednol dicloacetate particles and a lactose-etiprednol dicloacetate blend.

The SEM (XL30FEG FEI-Philips) procedure was conducted as briefly described below.

To obtain the SEM photographs, the powder sample was dusted onto the surface of individual aluminium stubs. The powder was then coated with a 20 nm layer of gold/palladium. Samples were observed in triplicate. Photomicrographs were taken at different magnifications (×100, ×200, ×750, ×2000) and subjected to image analysis (shortest, longest axis and mean aspect ratio). The photomicrographs are used to describe the morphology of the particles.

FIG. 1 shows a scanning electron microscopy (SEM) photograph of micronized etiprednol dicloacetate particles that passed through a 250 μm mesh. It is clearly shown that the drug particles exist as near spherical agglomerates.

FIG. 2 shows the scanning electron microscopy (SEM) photographs of a blend containing ca. 4.5% etiprednol dicloacetate in lactose monohydrate. The large crystals with predominantly “tomahawk” shape are alpha-lactose monohydrate. It is clearly shown that the etiprednol dicloacetate exists as primary particles of less than 50 μm, indicating that the original loose agglomerates of the active ingredient have broken down after blending with the excipient.

Example 6

This examples studies the effect of different agglomerate sizes of salbutamol sulphate and mixing time on the pharmaceutical performance of the powder.

This example describes a three-stage process. Stage 1 involves the sieving of the salbutamol sulphate agglomerates, stage 2 identifies optimal mixing times for this drug at two different agglomerate sizes for the production of a homogeneous mixture, and stage 3 demonstrates the effect of different agglomerate sizes and mixing times on the pharmacological profile of the drug.

Stage 1

Lactose was sieved using Alpine air jet sieving to give a particle size of 75-100 μm. The salbutamol sulphate agglomerates were sieved using sieves having a mesh size of 250 μm or 355 μm.

Stage 2

Six formulations were prepared as shown in Table 6.

TABLE 6

Formulations and mixing methods.

| Tumbling mixing 22 rpm | Tumbling mixing 46 rpm | Shear mixing ~1400 rpm |
|---|---|---|
| Formulation 1 1% salbutamol sulphate (<250 μm) blended with lactose | Formulation 3 1% salbutamol sulphate (<250 μm) blended with lactose | Formulation 5 1% salbutamol sulphate (<250 μm) blended with lactose |
| Formulation 2 1% salbutamol sulphate (<355 μm) blended with lactose | Formulation 4 1% salbutamol sulphate (<355 μm) blended with lactose | Formulation 6 1% salbutamol sulphate (<355 μm) blended with lactose |

Six samples were taken from the powder bed at 1, 3, 5, 10, 15, 20 and 30 minutes of mixing. 30 mg of each sample was dissolved and made up to 50 ml in methanol:water (50:50). The samples were assayed using a UV spectrophotometer at $\lambda_{max}=278$ nm to test for content homogeneity. The % w/w of blend strength and % RSD was determined. FIG. 3(a)-(f) shows the results for formulations 1-6.

The results show that when the formulations were mixed in the Turbula mixer, demixing of the formulation occurs when mixing time is prolonged. Excessive mixing should therefore be avoided to provide an optimal mixing time of the formulations to produce a homogeneous mixture. In addition, the greater the rotation speed of the Turbula mixer, the greater the deaggregation of the drug particles. Hence, 5 mins of mixing with a Turbula mixer at 46 rpm of formulations containing salbutamol sulphate <250 μm can produce formulations of acceptable homogeneity compared to 10 mins with Turbula mixer 22 rpm for salbutamol sulphate <250 μm. The high velocity of shear mixing provides the energy required to produce the rapid dispersion of drug particles such that a homogeneous mixture is formed more quickly.

Stage 3

The six formulations (from Table 6) were prepared again, but mixed at 15 and 5 minutes in the Turbula and Shear mixer, respectively. The formulations were tested for their in vitro deposition using a Twin Stage Impinger (TSI).

The homogeneity of formulation at the optimal mixing times was confirmed, as shown in Table 7.

TABLE 7

The homogeneity of formulations 1-6 at the optimal mixing times.

| Formulation (see Table 6) | Mixing time (min) | % w/w of recovered salbutamol sulphate | % RSD |
|---|---|---|---|
| 1 | 15 | 1.01 | 2.08 |
| 2 | 15 | 1.12 | 6.55 |
| 3 | 15 | 1.11 | 1.92 |
| 4 | 15 | 1.17 | 4.94 |
| 5 | 5 | 1.12 | 4.84 |
| 6 | 5 | 1.10 | 4.31 |

The TSI was actuated 20 times with a flow rate of 60 l/min, repeated six times for each formulation. Each stage of the TSI was rinsed with methanol:water (50:50), and the samples collected were assayed using a UV spectrophotometer at $\lambda_{max}=278$ nm. The fine particle fraction (FPF) was defined as the % of drug deposited in the lower stage compared to the total drug delivered. A comparison of % FPF between the different formulations shown in Table 8.

TABLE 8

A comparison of % FPF between the different formulations.

| Mixing mechanism | Agglomerate size of salbutamol sulphate (μm) | % FPF |
|---|---|---|
| Turbula 22 rpm | <250 | 43.61 |
| Turbula 22 rpm | <355 | 43.61 |
| Turbula 46 rpm | <250 | 38.47 |
| Turbula 46 rpm | <355 | 42.20 |
| Shear ~1400 rpm | <250 | 31.15 |
| Shear ~1400 rpm | <355 | 38.76 |

Thus, formulations containing salbutamol sulphate agglomerates of <355 um produce significantly higher FPF compared to the agglomerates of size <250 um for Shear mixing and Turbula mixing at 46 rpm but not for tumbler mixing at 22 rpm.

Figure 1:
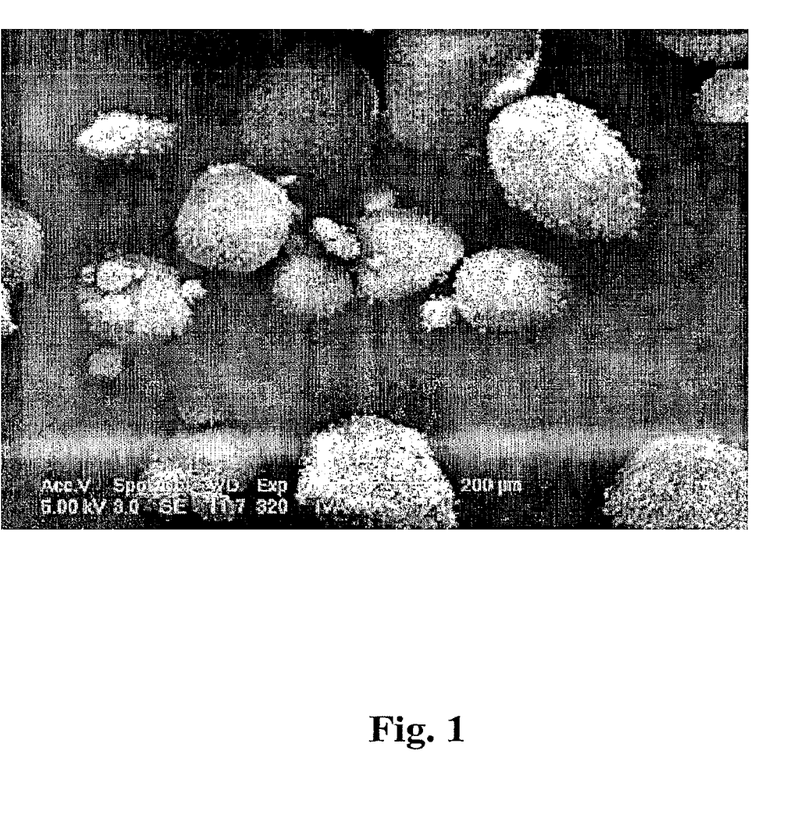
FIG. 1 is a scanning electron micrograph of micronised etiprednol dicloacetate particles after controlled agglomeration.
Figure 2:
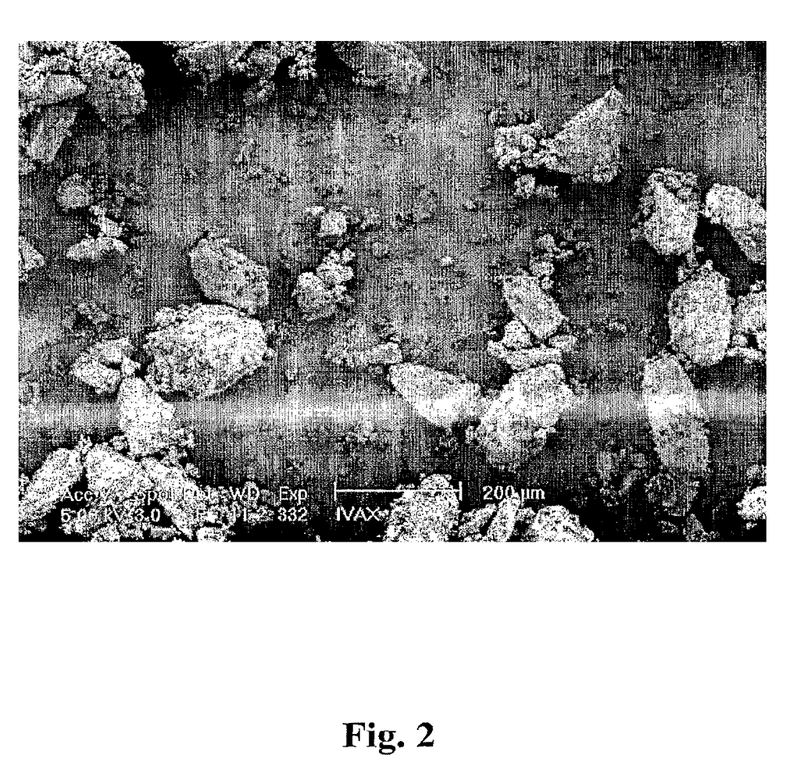
FIG. 2 is a scanning electron micrograph of a lactose-etiprednol dicloacetate blend showing that etiprednol dicloacetate has broken down into primary particles with a particle size of 50 μm or less.
Figure 3:
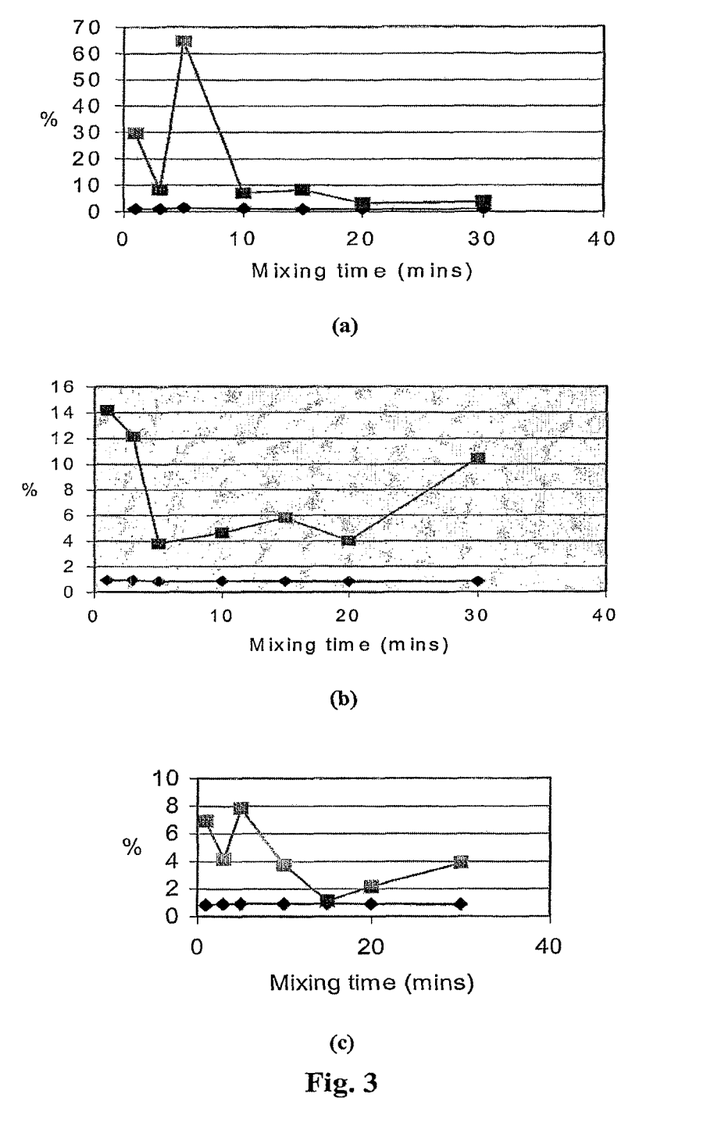
FIG. 3 is a graphical representation of the effect of mixing conditions on sample homogeneity.
Figure 4:
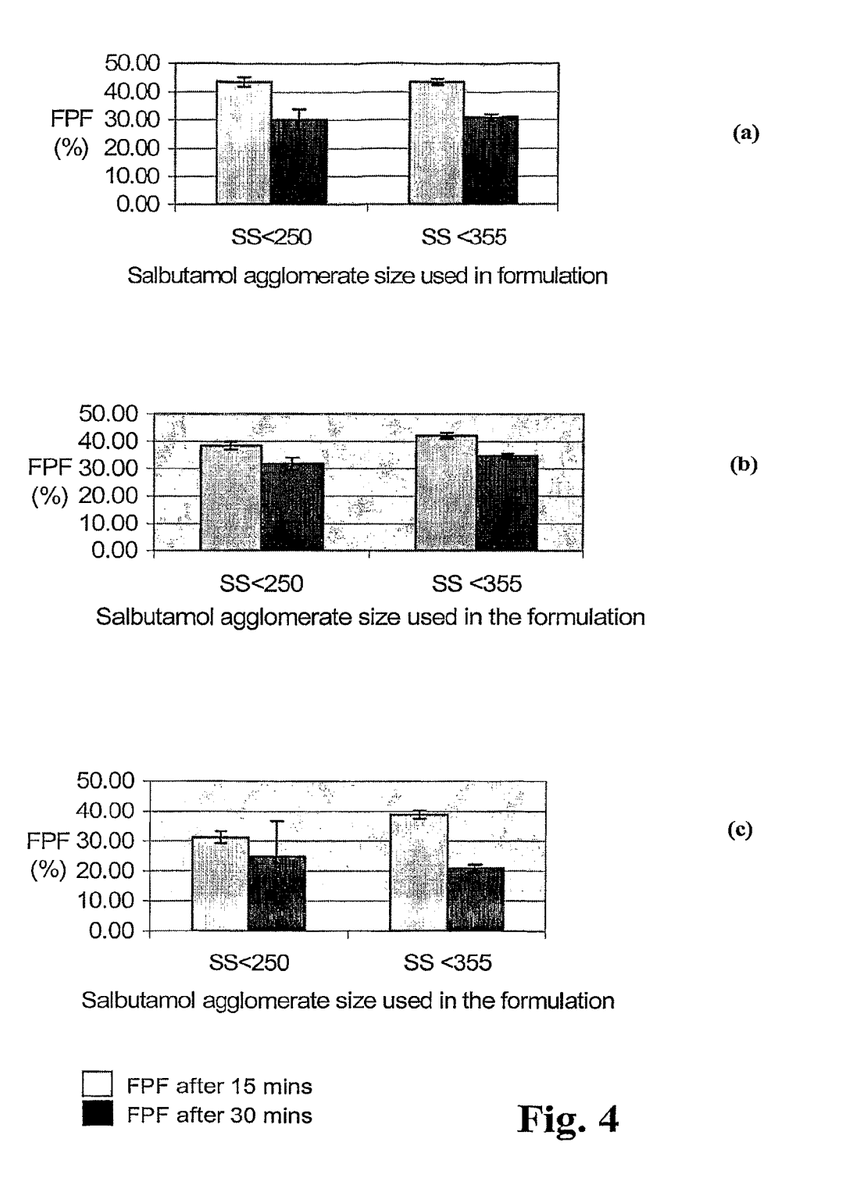
FIG. 4 is a graphical representation of the effect of mixing conditions on the fine particle fraction.

The FPF of the formulations which were mixed for a total of 30 minutes in stage 2 of the investigation were also tested for their in vitro deposition. The results were compared to the formulations mixed for 15 and 5 minutes for the Turbula and Shear mixer, respectively. FIG. 4 shows the effect of mixing time of FPF in a TSI for (a) Turbula mixing at 22 rpm, (b) Turbula mixing 46 rpm, and (c) Magimix Shear mixing at about 1400 rpm. The error bar represents the standard deviation. The results show that increasing the mixing time reduces the FPF.

Thus, 15 mins of mixing of the formulations with Turbula mixer and 5 mins of mixing using the Shear mixer produced a homogeneous formulation. The formulations containing the agglomerates of salbutamol sulphate <355 μm produced a significantly higher FPF than the formulation with salbutamol sulphate <250 μm using Turbula mixer at 46 rpm and a Shear mixer at ~1400 rpm.

EQUIVALENTS

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

The invention claimed is:

1. An inhalable medicament prepared by a process comprising the steps of:
  (a) forming a plurality of loose agglomerates of a pharmaceutically active ingredient by passing the pharmaceutically active ingredient through a sieve having a mesh of 50-3000 μm, wherein the loose agglomerates are not spheronized;
  (b) combining the plurality of loose agglomerates obtained from step (a) with a pharmaceutically acceptable particulate carrier; and
  (c) mixing the resultant material from step (b) in a mixer outside of an inhaler to break up the loose agglomerates into primary particles of the pharmaceutically active ingredient and to disperse the primary particles in the pharmaceutically acceptable particulate carrier such that 90% or more of the pharmaceutically active ingredient has a particle size of 50 µm or less to provide the inhalable medicament;

wherein the pharmaceutically active ingredient is selected from the group consisting of epinephrine, metaproterenol, terbutaline, albuterol, ipratropium bromide, aminophylline, dyphylline, flunisolide, beclomethasone, salmeterol and any isomers thereof.

2. The inhalable medicament of claim 1, wherein the pharmaceutically acceptable particulate carrier comprises lactose.

3. The inhalable medicament of claim 2, wherein the lactose is alpha-lactose monohydrate.

4. The inhalable medicament of claim 1, wherein the agglomerate particle size is such that the agglomerate is capable of passing through a sieve having a mesh of 250-1000 µm.

5. The inhalable medicament of claim 4, wherein in step (a) the pharmaceutically active ingredient is passed through a sieve having a mesh of 250-1000 µm.

6. The inhalable medicament of claim 1, wherein in step (c), the pharmaceutically active ingredient is dispersed homogenously in the pharmaceutically acceptable particulate carrier such that drug recovery from each of a plurality of samples taken from the medicament has a relative standard deviation from the mean of less than or equal to 5%.

7. A process for preparing a dry powder inhaler containing an inhalable medicament comprising the steps of:
   (a) forming a plurality of loose agglomerates of a pharmaceutically active ingredient by passing the pharmaceutically active ingredient through a sieve having a mesh of 50-3000 µm, wherein the loose agglomerates are not spheronized;
   (b) combining the plurality of loose agglomerates obtained from step (a) with a pharmaceutically acceptable particulate carrier;
   (c) mixing the resultant material from step (b) in a mixer outside of an inhaler to break up the loose agglomerates into primary particles of the pharmaceutically active ingredient and to disperse the primary particles in the pharmaceutically acceptable particulate carrier such that 90% or more of the pharmaceutically active ingredient has a particle size of 50 µm or less to provide the inhalable medicament; and
   (d) filling the inhalable medicament from step (c) into the reservoir of a dry powder inhaler;

wherein the pharmaceutically active ingredient is selected from the group consisting of epinephrine, metaproterenol, terbutaline, albuterol, ipratropium bromide, aminophylline, dyphylline, flunisolide, beclomethasone, salmeterol and any isomers thereof.

8. The process of claim 7, wherein the pharmaceutically acceptable particulate carrier comprises lactose.

9. The process of claim 8, wherein the lactose is alpha-lactose monohydrate.

10. The process of claim 7, wherein the agglomerate particle size is such that the agglomerate is capable of passing through a sieve having a mesh of 250-1000 µm.

11. The process of claim 10, wherein in step (a) the pharmaceutically active ingredient is passed through a sieve having a mesh of 250-1000 µm.

12. The process of claim 7, wherein in step (c), the pharmaceutically active ingredient is dispersed homogenously in the pharmaceutically acceptable particulate carrier such that drug recovery from each of a plurality of samples taken from the medicament has a relative standard deviation from the mean of less than or equal to 5%.

* * * * *